(12) United States Patent
Lange et al.

(10) Patent No.: US 7,319,110 B2
(45) Date of Patent: Jan. 15, 2008

(54) 1H-1,2,4-TRIAZOLE-3-CARBOXAMIDE DERIVATIVES HAVING CANNABINOID-CB$_1$ RECEPTOR AGONISTIC, PARTIAL AGONISTIC, INVERSE AGONISTIC OR ANTAGONISTIC ACTIVITY

(75) Inventors: Josephus H. M. Lange, Weesp (NL); Cornelis G. Kruse, Weesp (NL); Andrew C. McCreary, Weesp (NL); Herman H. van Stuivenberg, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 585 days.

(21) Appl. No.: 10/662,477

(22) Filed: Sep. 16, 2003

(65) Prior Publication Data
US 2004/0106614 A1 Jun. 3, 2004

(30) Foreign Application Priority Data
Sep. 19, 2002 (EP) .................................. 02078966

(51) Int. Cl.
*A61K 31/41* (2006.01)
*C07D 249/08* (2006.01)

(52) U.S. Cl. .................................... 514/383; 548/262.2
(58) Field of Classification Search ....................... None
See application file for complete search history.

(56) References Cited

U.S. PATENT DOCUMENTS 4,795,484 A * 1/1989 Aoki et al. .................. 504/273
5,624,941 A 4/1997 Barth et al.

FOREIGN PATENT DOCUMENTS

| WO | WO 01 29007 A1 | 4/2001 |
| WO | WO 01/29007 A1 | 4/2001 |
| WO | WO 01 58869 A2 | 8/2001 |
| WO | WO 01/58869 A2 | 8/2001 |

OTHER PUBLICATIONS

Jagerovic, N. et al., "A Novel Class of Heterocyclic Cannabinoids: Design, Preparation, In Vitro and In Vivo Studies of 1,2,4-Triazoles", Drugs Fut 2002, vol. 27 (Suppl. A): XVII$^{th}$ Int. Symp. on Medical Chemistry, pp. 271, (2002).
Harhash, A. H. et al., "Reactions of 2-Aryl-4-arylhdrazonon$^{-\Delta2-}$ oxazonlin-5-ones with Acid Amides & Diamines", Indian Journal of Chemistry, vol. 14B, pp. 268-272, (Apr. 1976).
Elnagdi, M. H. et al., "Studies with Polyfunctionally Substituted Heteroaromatics: 2-Phenyl-4-p-Tolylhydrazono-2-oxazoline-5-one as a Precursor for the Synthesis of Substituted 1,2,4-Triazoles and Pyridines", Heteroatom Chemistry, vol. 6, No. 6, pp. 589-592, (1995).
Clerin, D. et al., "No. 42.—Hétérocyclisation des α-acylaminoamides. III—Propriétés des amino-5 oxazoles", Bull. Soc. Chim. Fr., No. 1-2, Pt.2, pp. 211-217, (1974).
Dyck, et al., "Potent Imidazole and Triazole CB$_1$ Receptor Antagonists Related to SR141716," *Bioorganic & Medicinal Chemistry Letters*, 14:1151-1154 (2004).
Harhash et al., "Reactions of 2-aryl-4-arylhydrazono-.DELTA. 2-oxazolin-5-ones with acid amides and diamines," XP002225874 Abstract, *6001 Chemical Abstracts*, 85(23) (1976).
Elnagdi et al., "Studies with Polyfunctionally Substituted Heteroaromatics: 2-phenyl-4-p-tolylhydrazono-2-oxazoline-5-one as a Precursor for the Synthesis of Substituted 1,2,4-Triazoles and Pyridines," XP-002225875 Abstract, *6001 Chemical Abstracts*, 124(17), (1996).
Jagerovic et al., "A Novel Class of Heterocyclic Cannabinoids: Design, Preparation, in vitro and in vivo Studies of 1,2,4-Triazoles," XP-001121041 Abstract, *Drugs Future* 27(Suppl. A): XVI$^{th}$ Int. Symp. on Medicinal Chemistry (2002).

* cited by examiner

Primary Examiner—Rebecca Anderson
Assistant Examiner—Susannah Chung
(74) Attorney, Agent, or Firm—Finnegan, Henderson, Farabow, Garrett & Dunner, L.L.P.

(57) ABSTRACT

The present invention relates to a group of 1H-1,2,4-triazole-3-carboxamide derivatives, to methods for the preparation of these compounds, and to pharmaceutical compositions containing at least one of these compounds as an active ingredient.

These 1H-1,2,4-triazole-3-carboxamide derivatives are potent cannabinoid-CB$_1$ receptor agonists, partial agonists, inverse agonists or antagonists, useful for the treatment of disorders involving cannabinoid neurotransmission.

The compounds have the general formula (I)

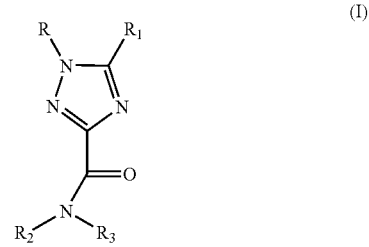

(I)

wherein R and R$_1$-R$_3$ have the meanings given in the specification.

4 Claims, No Drawings

1H-1,2,4-TRIAZOLE-3-CARBOXAMIDE DERIVATIVES HAVING CANNABINOID-CB₁ RECEPTOR AGONISTIC, PARTIAL AGONISTIC, INVERSE AGONISTIC OR ANTAGONISTIC ACTIVITY

The present invention relates to a group of 1H-1,2,4-triazole derivatives, to methods for the preparation of these compounds, and to pharmaceutical compositions containing one or more of these compounds as an active ingredient.

These 1H-1,2,4-triazole-carboxamide derivatives are potent cannabinoid-$CB_1$ receptor agonists, partial agonists, inverse agonists or antagonists, useful for the treatment of psychiatric and neurological disorders, as well as other diseases involving cannabinoid-$CB_1$ neurotransmission.

1,5-Diaryl-1H-1,2,4-triazole-3-carboxamide derivatives have been described in EP 0346620 and GB 2120665 as herbicides. Recently 1,2,4-triazoles were described as potential agonists and antagonists of cannabinoid-$CB_1$ and -$CB_2$ receptors (Jagerovic, N. et al., *Drugs Fut.* 2002, 27(Suppl. A): XVIIth Int. Symp. on Medicinal Chemistry, P284)

It has now surprisingly been found that known and new 1,5-diaryl-1H-1,2,4-triazole-3-carboxamide derivatives of the formula (I), as well as prodrugs, salts, and stereo-isomers thereof, are potent antagonists, agonists, inverse agonists or partial agonists of the cannabinoid $CB_1$ receptor:

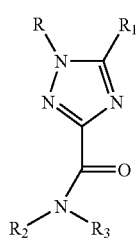

(I)

wherein

R and $R_1$ independently represent a phenyl, naphtyl, thienyl, pyridyl, pyrimidyl, pyrazinyl, pyridazinyl or triazinyl group, which groups may be substituted with 1-4 substituents X, which can be the same or different, from the group branched or unbranched $(C_{1-3})$-alkyl or alkoxy, hydroxy, halogen, trifluoromethyl, trifluoromethylthio, trifluoromethoxy, nitro, amino, mono- or dialkyl $(C_{1-2})$-amino, mono- or dialkyl $(C_{1-2})$-amido, $(C_{1-3})$-alkoxycarbonyl, trifluoromethylsulfonyl, sulfamoyl, $(C_{1-3})$-alkylsulfonyl, carboxyl, cyano, carbamoyl, $(C_{1-3})$-dialkylaminosulfonyl, $(C_{1-3})$-monoalkylamino-sulfonyl and acetyl, $R_2$ represents a hydrogen atom or a branched or unbranched $C_{1-8}$ alkyl or $C_{1-8}$ cycloalkyl-alkyl group or a phenyl, benzyl or phenethyl group which aromatic rings may be substituted with 1-4 substituents X, wherein X has the meaning as indicated above, or $R_2$ represents a pyridyl or thienyl group, $R_3$ represents branched or unbranched $C_{1-8}$ alkyl, $C_{1-8}$ alkoxy, $C_{3-8}$ cycloalkyl, $C_{5-10}$ bicycloalkyl, $C_{6-10}$ tricycloalkyl, $C_{3-8}$ alkenyl, $C_{5-8}$ cycloalkenyl, which groups may optionally contain one or more heteroatoms from the group (O, N, S), which groups may be substituted with a hydroxy group, an ethynyl group or 1-3 fluoro atoms, or $R_3$ represents a phenyl, benzyl or phenethyl group which aromatic rings may be substituted with 1-4 substituents X, wherein X has the meaning as indicated above, or $R_3$ represents a pyridyl, pyrimidyl, pyrazinyl, pyridazinyl, triazinyl or thienyl group which heteroaromatic rings may be substituted with 1-2 substituents X, wherein X has the meaning as indicated above, or $R_3$ represents a group $NR_4R_5$ wherein $R_4$ and $R_5$, together with the nitrogen atom to which they are bonded, form a saturated or unsaturated, monocyclic or bicyclic, heterocyclic moiety having 4 to 10 ring atoms, which heterocyclic group contains one or two heteroatoms from the group N, O or S, which heteroatoms can be the same or different, which heterocyclic moiety may be substituted with a branched or unbranched $C_{1-3}$ alkyl, hydroxy or trifluoromethyl group or a fluoro atom, or $R_2$ and $R_3$, together with the nitrogen atom to which they are bonded, form a saturated or unsaturated, monocyclic or bicyclic, heterocyclic moiety having 4 to 10 ring atoms, which heterocyclic group contains one or two heteroatoms from the group N, O or S, which heteroatoms can be the same or different, which heterocyclic moiety may be substituted with a branched or unbranched $C_{1-3}$ alkyl, hydroxy, piperidinyl or trifluoromethyl group or a fluoro atom.

A group of four 1,5-diaryl-1H-1,2,4-triazole-3-carboxamide derivatives in which the amide N-atom is part of an unsubstituted piperidinyl or morpholinyl group is described by D. Clerin and J. P. Fleury in *Bull. Soc. Chim. Fr.*, 1974, 1-2, Pt.2, 211-217.

1-(4-Methylphenyl)-5-phenyl-N-(2-pyridyl)-1H-1,2,4-triazole-3-carboxamide is described by M. H. Elnagdi et al. in *Heteroatom Chem.*, 1995, 6, 589-592.

A group of four 1,5-diaryl-N-(2-pyridyl)-1H-1,2,4-triazole-3-carboxamides is described by A. H. Harhash et al. in *Indian J. Chem.*, 1976, 14B, 268-272.

Due to the potent cannabinoid-$CB_1$ receptor agonistic, partial agonistic, inverse agonistic or antagonistic activity the compounds of the invention are suitable for use in the treatment of psychosis, anxiety, depression, attention deficits, memory disorders, cognitive disorders, appetite disorders, obesity, addiction, appetence, drug dependence, neurodegenerative disorders, dementia, dystonia, muscle spasticity, tremor, epilepsy, multiple sclerosis, traumatic brain injury, stroke, Parkinson's disease, Alzheimer's disease, epilepsy, Huntington's disease, Tourette's syndrome, cerebral ischaemia, cerebral apoplexy, craniocerebral trauma, stroke, spinal cord injury, neuroinflammatory disorders, plaque sclerosis, viral encephalitis, demyelinisation related disorders, as well as for the treatment of pain disorders, including neuropathic pain disorders, septic shock, glaucoma, diabetes, cancer, emesis, nausea, gastrointestinal disorders, gastric ulcers, diarrhoea and cardiovascular disorders.

The affinity of the compounds of the invention for cannabinoid $CB_1$ receptors was determined using membrane preparations of Chinese hamster ovary (CHO) cells in which the human cannabinoid $CB_1$ receptor is stably transfected in conjunction with [³H]CP-55,940 as radioligand. After incubation of a freshly prepared cell membrane preparation with the [³H]-ligand, with or without addition of compounds of the invention, separation of bound and free ligand was performed by filtration over glassfiber filters. Radioactivity on the filter was measured by liquid scintillation counting.

The cannabinoid $CB_1$ receptor antagonistic, agonistic or partial agonistic activity of compounds of the invention was determined by functional studies using the human $CB_1$ receptor cloned in Chinese hamster ovary (CHO) cells. CHO cells were grown in a DMEM culture medium, supplemented with 10% heat-inactivated fetal calf serum. Medium was aspirated and replaced by DMEM, without fetal calf serum, but containing [$^3$H]-Arachidonic acid and incubated overnight in a cell culture stove (5% $CO_2$/95% air; 37° C.; water-saturated atmosphere). During this period [$^3$H]-Arachidonic acid was incorporated in membrane phospholipids. On the test day, medium was aspirated and cells were washed three times using 0.5 ml phosphate-buffered saline, containing 0.2% bovine serum albumin. Stimulation of the $CB_1$ receptor by WIN 55,212-2 led to activation of $PLA_2$ followed by release of [$^3$H]-Arachidonic acid into the medium. This WIN 55,212-2-induced release was concentration-dependently antagonized by $CB_1$ receptor antagonists.

Cannabinoid agonistic or partial agonistic activity of compounds of the invention can be determined according to published methods, such as assessment of in vivo cannabimimetic effects (Wiley, J. L.; Jefferson, R. G; Grier, M. C.; Mahadevan, A.; Razdan, R. K.; Martin, B. R. *J. Pharmacol. Exp. Ther.* 2001, 296, 1013).

The invention relates both to racemates, mixtures of diastereomers and the individual stereoisomers of the compounds having formula (I). Also prodrugs, i.e. compounds which when administered to humans by any known route, are metabolised to compounds having formula (I), belong to the invention. In particular this relates to compounds with primary or secondary amino or hydroxy groups. Such compounds can be reacted with organic acids to yield compounds having formula (I) wherein an additional group is present which is easily removed after administration, for instance, but not limited to amidine, enamine, a Mannich base, a hydroxyl-methylene derivative, an O-(acyloxymethylenecarbamate) derivative, carbamate, ester, amide or enaminone. A pro-drug is an inactive compound, which when absorbed is converted into an active form (Medicinal Chemistry: Principles and Practice, 1994, ISBN 0-85186-494-5, Ed.: F. D. King, p. 216).

The compounds of the invention can be brought into forms suitable for administration by means of usual processes using auxiliary substances and/or liquid or solid carrier materials.

Suitable synthetic routes for the compounds of the invention are the following:

Synthetic Route A

Step 1: Ester hydrolysis of a compound having formula (II) wherein $R_6$ represents a branched or unbranched ($C_{1-4}$)-alkyl group or a benzyl group,

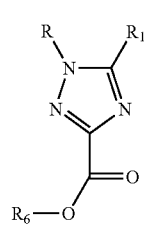

(II)

yields a compound having formula (III)

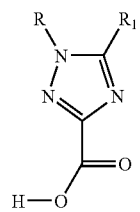

(III)

wherein R and $R_1$ have the meanings as described above.

The compounds of the invention having formula (II), wherein $R_6$ represents a branched or unbranched alkyl group ($C_{1-4}$) or benzyl group can be obtained according to methods known, for example:

a) Sawdey, G. W. *J. Am. Chem. Soc.* 1957, 79, 1955
b) Czollner, L. et al., *Arch. Pharm. (Weinheim)* 1990, 323, 225
c) Eicher, T. and Hauptmann, S. *The Chemistry of Heterocycles*, Thieme Verlag, Stuttgart, 1995 (ISBN 313 100511 4), p. 208-212.

Step 2: Reaction of a compound having formula (III) with a compound having formula $R_2R_3NH$ wherein $R_2$ and $R_3$ have the meanings as described above via activating and coupling methods such as formation of an active ester, or in the presence of a coupling reagent such as DCC, HBTU, BOP, CIP (2-chloro-1,3-dimethylimidazolinium hexafluorophosphate) or PyAOP (7-azabenzotriazol-1-yloxytris(pyrrolidino)phosphonium hexafluorophosphate). Activating and coupling methods of this type are described in a) M. Bodanszky and A. Bodanszky: *The Practice of Peptide Synthesis*, Springer-Verlag, New York, 1994; ISBN: 0-387-57505-7;
b) K. Akaji et al., *Tetrahedron Lett.* (1994), 35, 3315-3318);
c) F. Albericio et al., *Tetrahedron Lett.* (1997), 38, 4853-4856).

This reaction gives a 1H-1,2,4-triazole derivative having formula (I).

Synthetic Route B

A compound having formula (III) is reacted with a halogenating agent such as thionyl chloride ($SOCl_2$) or oxalyl chloride. This reaction yields the corresponding carbonyl chloride (acid chloride) (IV).

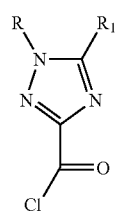

(IV)

Reaction of a compound having formula (IV) with a compound having formula $R_2R_3NH$ wherein wherein $R_2$ and $R_3$ have the meanings as described above gives a 1H-1,2,4-triazole derivative having formula (I).

Synthetic Route C

A compound having formula (II) is reacted in an amidation reaction with a compound having formula $R_2R_3NH$ wherein $R_2$ and $R_3$ have the meanings as described hereinabove to give a 1H-1,2,4-triazole derivative having formula (I). Such amidation reactions can be promoted by the use of trimethylaluminum Al(CH$_3$)$_3$ (For more information on aluminum-mediated conversion of esters to amides, see: J. I. Levin, E. Turos, S. M. Weinreb, *Synth Commun.* (1982), 12, 989-993.)

EXAMPLE I

Part A: To a stirred solution of dimethyl aminomalonate hydrochloride (25 gram, 0.136 mol) in dichloromethane (200 mL) triethylamine (41.4 mL, 2.2 molar equivalent) is added at 0° C. 4-Chlorobenzoyl chloride (23.8 gram, 0.136 mol) is slowly added and the resulting solution is allowed to stand at room temperature overnight. Water is added and the organic layer is separated. The water layer is extracted twice with dichloromethane. The collected organic layers are washed with water, dried over MgSO$_4$, filtered and concentrated in vacuo. The residue is recrystallised from methanol (400 mL) to give dimethyl 2-(4-chlorobenzoylamino)malonate (30.5 gram, 79% yield). Melting point: 146-148° C. $^1$H-NMR (200 MHz, CDCl$_3$): δ 3.86 (s, 6H), 5.38 (d, J=6 Hz, 1H), 7.15 (br d, J~6 Hz, 1H), 7.43 (d, J=8 Hz, 2H), 7.79 (d, J=8 Hz, 2H).

Part B: To a stirred suspension of 2,4-dichloroaniline (19.44 gram, 0.12 mol) in concentrated HCl (25 mL) and acetic acid (75 mL) at 0° C. is added a solution of NaNO$_2$ (9.0 gram, 0.13 mol) in water (50 mL) and the resulting solution is stirred for 15 minutes. A solution of dimethyl 2-(4-chlorobenzoylamino)malonate (28.55 gram, 0.10 mol) in acetone (200 mL) is slowly added while keeping the temperature below 0° C. A solution of K$_2$CO$_3$ (120 gram) in water (200 mL) is slowly added and the resulting black mixture is stirred for 30 minutes at 0° C. The mixture is extracted three times with EtOAc. The collected organics are washed with water, aqueous NaHCO$_3$ and water, respectively, dried over MgSO$_4$, filtered and concentrated in vacuo. The residue is dissolved in methanol (500 mL) and a solution of sodium (1 gram) in methanol (75 mL) is added. The resulting stirred mixture is allowed to stand overnight at room temperature and cooled in a refrigerator. The formed precipitate is collected by filtration and washed with methanol to give methyl 5-(4-chlorophenyl)-1-(2,4-dichlorophenyl)-1H-1,2,4-triazole-3-carboxylate (11.4 gram, 30% yield). Melting point: 153-154° C. $^1$H-NMR (200 MHz, CDCl$_3$): δ 4.07 (s, 3H), 7.28-7.60 (m, 7H).

Part C: To a stirred suspension of methyl 5-(4-chlorophenyl)-1-(2,4-dichlorophenyl)-1H-1,2,4-triazole-3-carboxylate (11.3 gram, 0.0295 mol) in methanol (100 mL) is added KOH (45% aqueous solution, 7.5 mL) and the resulting mixture is heated at reflux temperature for 4 hours. The mixture is concentrated in vacuo and water (150 mL) and concentrated HCl are added. The yellow precipitate is collected by filtration, washed with water and dried in vacuo to give 5-(4-chlorophenyl)-1-(2,4-dichlorophenyl)-1H-1,2,4-triazole-3-carboxylic acid (10.0 gram, 92% yield). Melting point: 141-144° C. (decomposition).

Part D: To a stirred solution of 5-(4-chlorophenyl)-1-(2,4-dichlorophenyl)-1H-1,2,4-triazole-3-carboxylic acid (1.48 gram, 4.0 mmol) in acetonitrile (20 mL) is successively added diisopropylethylamine (DIPEA) (1.5 mL, 2.1 molar equivalent), O-benzotriazol-1-yl-N,N, N',N'-tetramethyluronium hexafluorophosphate (HBTU) (1.66 gram, 1.1 molar equivalent) and 1-aminopiperidine (0.44 gram, 1.1 molar equivalent). After stirring overnight an aqueous NaHCO$_3$ solution is added. The resulting mixture is three times extracted with dichloromethane. The combined organic layers are washed with water, dried over Na$_2$SO$_4$, filtered and concentrated in vacuo to give a crude oil (3.6 gram). This oil is further purified by flash chromatography (silica gel; EtOAc/petroleum ether (40-60° C.)=7/3 (v/v)). The purified material is treated with ethanolic HCl (1M solution) to give 5-(4-chlorophenyl)-1-(2,4-dichlorophenyl)-N-(piperidin-1-yl)-1H-1,2,4-triazole-3-carboxamide hydrochloride (1.50 gram, 77% yield). Melting point: 238-240° C. (decomposition). $^1$H-NMR (400 MHz, DMSO-d$_6$): δ 1.46-1.54 (m, 2H), 1.78-1.85 (m, 4H), 3.22-3.28 (m, 4H), 7.50 (s, 4H), 7.70 (dd, J=8 and 2 Hz, 1H), 7.85-7.87 (m, 1H), 7.91 (d, J=8 Hz, 1H), (NH not visible).

Analogously were prepared the examples 2-18:

2. 5-(4-Chlorophenyl)-1-(2,4-dichlorophenyl)-N-(pyrrolidin-1-yl)-1H-1,2,4-triazole-3-carboxamide hydrochloride. Melting point: 248-255° C. (decomposition).
3. 5-(4-Chlorophenyl)-N-cyclohexyl-1-(2,4-dichlorophenyl)-1H-1,2,4-triazole-3-carboxamide. Melting point: 186-188° C.
4. N-t-Butoxy-5-(4-chlorophenyl)-1-(2,4-dichlorophenyl)-1H-1,2,4-triazole-3-carboxamide. Melting point: 150-152° C.
5. 5-(4-Chlorophenyl)-1-(2,4-dichlorophenyl)-N-(n-pentyl)-1H-1,2,4-triazole-3-carboxamide. $^1$H-NMR (400 MHz, CDCl$_3$): δ 0.92 (t, J=7 Hz, 3H), 1.35-1.44 (m, 4H), 1.62-1.70 (m, 2H), 3.48-3.56 (m, 2H), 7.20-7.25 (m, 1H), 7.34 (dt, J=8 and 2 Hz, 2H), 7.42-7.50 (m, 4H), 7.54 (d, J=2 Hz, 1H).
6. 5-(4-Chlorophenyl)-1-(2,4-dichlorophenyl)-N-(morpholin-4-yl)-1H-1,2,4-triazole-3-carboxamide. Melting point: 184-186° C.
7. 1-(4-Chlorophenyl)-5-(2,4-dichlorophenyl)-N-(piperidin-1-yl)-1H-1,2,4-triazole-3-carboxamide hydrochloride. Melting point: 234-237° C. (decomposition).
8. 1-(4-Chlorophenyl)-5-(2,4-dichlorophenyl)-N-(pyrrolidin-1-yl)-1H-1,2,4-triazole-3-carboxamide hydrochloride. Melting point: 234-236° C. (decomposition).
9. 1-(4-Chlorophenyl)-N-cyclohexyl-5-(2,4-dichlorophenyl)-1H-1,2,4-triazole-3-carboxamide. $^1$H-NMR (400 MHz, CDCl$_3$): δ 1.14-1.81 (m, 8H), 2.02-2.10 (m, 2H), 4.00-4.11 (m, 1H), 7.08 (br d, J~7 Hz, 1H), 7.26 (br d, J~8 Hz, 2H), 7.34 (br d, J~8 Hz, 2H), 7.40 (dd, J=8 and 2 Hz, 1H), 7.44-7.48 (m, 2H).
10. N-t-Butoxy-1-(4-chlorophenyl)-5-(2,4-dichlorophenyl)-1H-1,2,4-triazole-3-carboxamide. $^1$H-NMR (400 MHz, CDCl$_3$): δ 1.38 (s, 9H), 7.25 (br d, J~8 Hz, 2H), 7.35 (br d, J~8 Hz, 2H), 7.41 (dd, J=8 and 2 Hz, 1H), 7.44-7.48 (m, 2H), 9.18, br s, 1H).
11. 1-(4-Chlorophenyl)-5-(2,4-dichlorophenyl)-N-(n-pentyl)-1H-1,2,4-triazole-3-carboxamide. $^1$H-NMR (400 MHz, CDCl$_3$): δ 0.91 (t, J=7 Hz, 3H), 1.35-1.41 (m, 4H), 1.60-1.70 (m, 2H), 3.48-3.56 (m, 2H), 7.21 (br t, J~7 Hz, 1H), 7.26 (br d, J~8 Hz, 2H), 7.34 (br d, J~8 Hz, 2H), 7.40 (dd, J=8 and 2 Hz, 1H), 7.44-7.48 (m, 2H).
12. 1-(4-Chlorophenyl)-5-(2,4-dichlorophenyl)-N-(morpholin-4-yl)-1H-1,2,4-triazole-3-carboxamide hydrochloride. Melting point: 224-226° C.
13. 1-(2,4-Dichlorophenyl)-5-(pyridin-2-yl)-N-(piperidin-1-yl)-1H-1,2,4-triazole-3-carboxamide. Melting point: 191-193° C.
14. 5-(2,4-Dichlorophenyl)-N-(piperidin-1-yl)-1-(4-(trifluoromethyl)phenyl)-1H-1,2,4-triazole-3-carboxamide. Melting point: 159-161° C.
15. 1'-[5-(2,4-dichlorophenyl)-1-(4-(trifluoromethyl)phenyl)-1H-1,2,4-triazol-3-yl)carbonyl]piperidine. Melting point: 155-156° C.

16. 1-(2,4-Dichlorophenyl)-N-(piperidin-1-yl)-5-(pyridin-3-yl)-1H-1,2,4-triazole-3-carboxamide. Melting point: 219° C.
17. 1-(4-Chlorophenyl)-5-(2,4-dichlorophenyl)-N-(5,5,5-trifluoropentyl)-1H-1,2,4-triazole-3-carboxamide. $^1$H-NMR (400 MHz, CDCl$_3$): δ1.63-1.80 (m, 4H), 2.06-2.22 (m, 2H), 3.54 (q, J~7 Hz, 2H), 7.26 (m, 3H), 7.34 (br d, J~8 Hz, 2H), 7.40 (dd, J=8 and 2 Hz, 1H), 7.44-7.48 (m, 2H).
18. 1-(4-Chlorophenyl)-5-(2,4-dichlorophenyl)-N-(5-fluoropentyl)-1H-1,2,4-triazole-3-carboxamide. $^1$H-NMR (400 MHz, CDCl$_3$): δ 1.63-1.80 (m, 4H), 2.06-2.22 (m, 2H), 3.54 (q, J~7 Hz, 2H), 7.22-7.28 (m, 3H), 7.34 (br d, J~8 Hz, 2H), 7.40 (dd, J=8 and 2 Hz, 1H), 7.44-7.48 (m, 2H).

EXAMPLE 19

Part A: 1-(Chlorophenyl)-5-(2,4-dichlorophenyl)-1H-1,2,4-triazole-3-carboxylic acid was prepared analogously to the procedure as described in Example 1, Part A-C by using dimethyl aminomalonate hydrochloride, 2,4-dichlorobenzoyl chloride and 4-chloroaniline as starting materials, respectively. Melting point: 102-104° C. $^1$H-NMR (400 MHz, DMSO-d$_6$): δ 7.36 (br d, J~8 Hz, 2H), 7.50 (br d, J~8 Hz, 2H), 7.59 (dd, J=8 and 2 Hz, 1H), 7.70 (d, J=2 Hz, 1H), 7.75 (d, J=8 Hz, 1H), OH proton is part of water peak at δ 3.4.

Analogously was 1-(chlorophenyl)-5-(2,5-dichlorophenyl)-1H-1,2,4-triazole-3-carboxylic acid prepared by using dimethyl aminomalonate hydrochloride, 2,5-dichlorobenzoyl chloride and 4-chloroaniline as starting materials, respectively. Melting point: 183-188° C. $^1$H-NMR (400 MHz, DMSO-d$_6$): δ 7.41 (br d, J~8 Hz, 2H), 7.52 (br d, J~8 Hz, 2H), 7.56 (d, J=8 Hz, 1H), 7.65 (dd, J=8 and 2 Hz, 1H), 7.88 (d, J=2 Hz, 1H), OH proton is part of water peak at δ 3.5.

Part B: To a stirred solution of 1-(chlorophenyl)-5-(2,4-dichlorophenyl)-1H-1,2,4-triazole-3-carboxylic acid (0.37 g, 1.00 mmol) in dichloromethane (10 mL) is added oxalyl chloride (0.254 g, 2.00 mmol). The resulting mixture is concentrated in vacuo to give crude 1-(chlorophenyl)-5-(2,4-dichlorophenyl)-1H-1,2,4-triazole-3-carbonyl chloride.

Part C: The crude 1-(chlorophenyl)-5-(2,4-dichlorophenyl)-1H-1,2,4-triazole-3-carbonyl chloride is dissolved in tetrahydrofuran (THF) (10 mL). 2,3-Dihydro-1H-inden-2-ylamine (0.40 g, 3.00 mmol) is added and the resulting solution is stirred for 42 hours at 25° C. The mixture is concentrated in vacuo and the residue is purified by preparative liquid chromatography to give pure 1-(4-chlorophenyl)-5-(2,4-dichlorophenyl)-N-(2,3-dihydro-1H-inden-2-yl)-1H-1,2,4-triazole-3-carboxamide (393 mg, 81% yield). MS (ESI$^+$) 485.6. $^1$H-NMR (400 MHz, DMSO-d$_6$): 3.06 (dd, J=16 and 8 Hz, 2H), 3.21 (dd, J=16 and 8 Hz, 2H), 4.71-4.82 (m, 1H), 7.12-7.16 (m, 2H), 7.19-7.24 (m. 2H), 7.39 (br d, J~8 Hz, 2H), 7.52 (br d, J~8 Hz, 2H), 7.60 (dd, J=8 and 2 Hz, 1H), 7.71 (d, J=2 Hz, 1H), 7.79 (d, J=8 Hz, 1H), 8.93-8.97 (m, 1H, NH).

Analogously were prepared the examples 20-43:
20. 1-(4-Chlorophenyl)-5-(2,4-dichlorophenyl)-N-(1-ethynylcyclohexyl)-1H-1,2,4-triazole-3-carboxamide. MS (ESI$^+$) 473.3.
21. 1-(4-Chlorophenyl)-5-(2,4-dichlorophenyl)-N-(2-methylcyclohexyl)-1H-1,2,4-triazole-3-carboxamide. MS (ESI$^+$) 465.5.
22. 1-(4-Chlorophenyl)-5-(2,4-dichlorophenyl)-N-(4-methylcyclohexyl)-1H-1,2,4-triazole-3-carboxamide. MS (ESI$^+$) 465.5.
23. 1-(4-Chlorophenyl)-5-(2,4-dichlorophenyl)-N-cyclooctyl-1H-1,2,4-triazole-3-carboxamide. MS (ESI$^+$) 477.3.
24. 1-(4-Chlorophenyl)-5-(2,4-dichlorophenyl)-N-(azepan-1-yl)-1H-1,2,4-triazole-3-carboxamide. MS (ESI$^+$) 466.4.
25. 1-(4-Chlorophenyl)-5-(2,4-dichlorophenyl)-N-cycloheptyl-1H-1,2,4-triazole-3-carboxamide. MS (ESI$^+$) 465.5.
26. N-t-Butyl-1-(4-chlorophenyl)-5-(2,4-dichlorophenyl)-1H-1,2,4-triazole-3-carboxamide. MS (ESI$^+$) 425.4.
27. 1-(4-Chlorophenyl)-5-(2,4-dichlorophenyl)-N-(1,1-diethylprop-2-yn-1-yl)-1H-1,2,4-triazole-3-carboxamide. MS (ESI$^+$) 461.5.
28. 1-(4-Chlorophenyl)-5-(2,4-dichlorophenyl)-N-(2,2,2-trifluoroethyl)-1H-1,2,4-triazole-3-carboxamide. MS (ESI$^+$) 451.3.
29. 1-(4-Chlorophenyl)-5-(2,4-dichlorophenyl)-N-(exo-bicyclo[2.2.1]hept-2-yl)-1H-1,2,4-triazole-3-carboxamide. MS (ESI$^+$) 461.5.
30. 1-(4-Chlorophenyl)-5-(2,4-dichlorophenyl)-N-(4-(2-propyl)piperazin-1-yl)-1H-1,2,4-triazole-3-carboxamide. MS (ESI$^+$) 480.3. $^1$H-NMR (400 MHz, DMSO-d$_6$): 1.00 (d, J=7 Hz, 6H), 2.46-2.56 (m, 4H), 2.72 (septet, J=7 Hz, 1H), 3.66-3.74 (m, 4H), 7.36 (br d, J=8 Hz, 2H), 7.51 (br d, J=8 Hz, 2H), 7.59 (dd, J=8 and 2 Hz, 1H), 7.72 (d, J=2 Hz, 1H), 7.75 (d, J=8 Hz, 1H).
31. 1-(4-Chlorophenyl)-5-(2,4-dichlorophenyl)-N-(hexahydrocyclopenta[c]pyrrol-2(1H)-yl)-1H-1,2,4-triazole-3-carboxamide. MS (ESI$^+$) 476.4.
32. 1-(4-Chlorophenyl)-5-(2,4-dichlorophenyl)-N-pentyl-1H-1,2,4-triazole-3-carboxamide. MS (ESI$^+$) 435.5.
33. 1-(4-Chlorophenyl)-5-(2,4-dichlorophenyl)-N-(2,2-dimethylpropyl)-1H-1,2,4-triazole-3-carboxamide. MS (ESI$^+$) 439.6.
34. 1-(4-Chlorophenyl)-5-(2,4-dichlorophenyl)-N-(3-(trifluoromethyl)phenyl)-1H-1,2,4-triazole-3-carboxamide. MS (ESI$^+$) 511.7.
35. 1'-[1-(4-Chlorophenyl)-5-(2,4-dichlorophenyl)-1H-1,2,4-triazol-3-yl)carbonyl]-1,4'-bipiperidine. MS (ESI$^+$) 520.5.
36. 1-(4-Chlorophenyl)-N-(4-chlorophenyl)-5-(2,5-dichlorophenyl)-N-methyl-1H-1,2,4-triazole-3-carboxamide. MS (ESI$^+$) 491.4.
37. 1-(4-Chlorophenyl)-5-(2,5-dichlorophenyl)-N-(1-ethynylcyclohexyl)-1H-1,2,4-triazole-3-carboxamide. MS (ESI$^+$) 473.4.
38. 1-(4-Chlorophenyl)-5-(2,5-dichlorophenyl)-N-(2-methylcyclohexyl)-1H-1,2,4-triazole-3-carboxamide. MS (ESI$^+$) 465.5.
39. 1-(4-Chlorophenyl)-5-(2,5-dichlorophenyl)-N-(4-methylcyclohexyl)-1H-1,2,4-triazole-3-carboxamide. MS (ESI$^+$) 465.6.
40. 1-(4-Chlorophenyl)-5-(2,5-dichlorophenyl)-N-cyclooctyl-1H-1,2,4-triazole-3-carboxamide. MS (ESI$^+$) 477.3.
41. 1-(4-Chlorophenyl)-5-(2,5-dichlorophenyl)-N-cycloheptyl-1H-1,2,4-triazole-3-carboxamide. MS (ESI$^+$) 465.6.
42. 1-(4-Chlorophenyl)-5-(2,5-dichlorophenyl)-N-cyclopentyl-1H-1,2,4-triazole-3-carboxamide. MS (ESI$^+$) 435.5.
43. 1-(4-Chlorophenyl)-5-(2,5-dichlorophenyl)-N-(2,2-dimethylpropyl)-1H-1,2,4-triazole-3-carboxamide. MS (ESI$^+$) 439.6.

Pharmacological test results of a subset of the compounds of the invention, obtained with the assays described above, are given in the table below:

| Example | Human cannabinoid-$CB_1$ receptors | |
| --- | --- | --- |
| | In vitro affinity $pK_i$ value | In vitro antagonism $pA_2$ value |
| Example 2 | 6.6 | 7.2 |
| Example 3 | 6.9 | 8.7 |
| Example 5 | 6.9 | |
| Example 9 | 7.4 | 8.2 |
| Example 11 | 6.3 | |

What is claimed is:

1. A compound of the Formula (I)

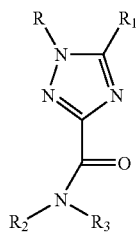

(I)

or a stereoisomer or a pharmacologically acceptable salt thereof, wherein:

R and $R_1$ independently represent a phenyl, naphtyl, thienyl, pyridyl, pyrimidyl, pyrazinyl, pyridazinyl or triazinyl group, which groups are optionally substituted with 1-4 substituents X, which can be the same or different, and are chosen from branched and unbranched ($C_{1-3}$)-alkyl and alkoxy, hydroxy, halogen, trifluoromethyl, trifluoromethylthio, trifluoromethoxy, nitro, amino, mono- and dialkyl ($C_{1-2}$)-amino, mono- and dialkyl ($C_{1-2}$)-amido, ($C_{1-3}$)-alkoxycarbonyl, trifluoromethylsulfonyl, sulfamoyl, ($C_{1-3}$)-alkylsulfonyl, carboxyl, cyano, carbamoyl, ($C_{1-3}$)-dialkylaminosulfonyl, ($C_{1-3}$)-monoalkylamino-sulfonyl and acetyl groups;

$R_2$ represents a hydrogen atom or a branched or unbranched $C_{1-8}$ alkyl group;

$R_3$ represents branched or unbranched, $C_{2-8}$ alkoxy, $C_{3-8}$ cycloalkyl, $C_{5-10}$ bicycloalkyl, $C_{6-10}$ tricycloalkyl, $C_{4-8}$ alkenyl, which groups may optionally contain one or more heteroatoms chosen from O, N, and S, which heteroatoms are optionally substituted with a hydroxy group or 1-3 fluoro atoms, or $R_3$ represents a $C_{3-8}$ trifluoroalkyl or $C_{2-8}$ fluoroalkyl group, or $R_3$ represents a benzyl or phenethyl group, which aromatic rings are optionally substituted with 1-4 substituents X, which can be the same or different, and are chosen from branched and unbranched ($C_{1-3}$)-alkyl and alkoxy, hydroxy, halogen, trifluoromethyl, trifluoromethylthio, trifluoromethoxy, nitro, mono- and dialkyl ($C_{1-2}$)-amino, ($C_{1-3}$)-alkoxycarbonyl, trifluoromethylsulfonyl, sulfamoyl, ($C_{1-3}$)-alkylsulfonyl, carboxyl, cyano, carbamoyl, ($C_{1-3}$)-dialkylaminosulfonyl, ($C_{1-3}$)-monoalkylaminosulfonyl and acetyl groups, or $R_3$ represents 3-pyridyl, 4-pyridyl, pyrimidyl, pyrazinyl, pyridazinyl, triazinyl or thienyl group, which heteroaromatic rings are optionally substituted with 1 or 2 substituents X, wherein X has the meaning as given above, or $R_3$ represents a group $NR_4R_5$, wherein $R_4$ and $R_5$, together with the nitrogen atom to which they are bonded, form a saturated or unsaturated, monocyclic or bicyclic, heterocyclic moiety having 4 to 10 ring atoms, which heterocyclic moeity contains one or two heteroatoms chosen from O, N, and S, which heteroatoms can be the same or different, and wherein the heterocyclic moiety is optionally substituted with a branched or unbranched $C_{1-3}$ alkyl, hydroxy or trifluoromethyl group or a fluoro atom, or $R_2$ and $R_3$, together with the nitrogen atom to which they are bonded, form a saturated or unsaturated, monocyclic or bicyclic, heterocyclic moiety having 4 to 10 ring atoms, which heterocyclic moiety contains one or two heteroatoms chosen from O, N, and S, which heteroatoms can be the same or different, and wherein the heterocyclic moiety is optionally substituted with a branched or unbranched $C_{1-3}$ alkyl, hydroxy, piperidinyl or trifluoromethyl group or a fluoro atom, with the proviso that this heterocyclic moiety is not an unsubstituted piperidinyl or unsubstituted morpholinyl group or 2,2,6,6-tetraalkylpiperidinyl group.

2. A compound as claimed in claim 1, and having Formula (I)

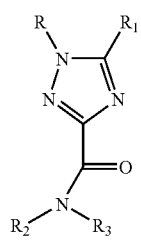

(I)

or a stereoisomer or pharmacologically acceptable salt thereof, wherein:

R and $R_1$ independently represent a phenyl, naphtyl, thienyl, pyridyl, pyrimidyl, pyrazinyl, pyridazinyl or triazinyl group, which groups are substituted with 1-4 substituents X, wherein X, which can be the same or different, and are chosen from branched and unbranched ($C_{1-3}$)-alkyl and alkoxy, hydroxy, halogen, trifluoromethyl, trifluoromethylthio, trifluoromethoxy, nitro, amino, mono- and dialkyl ($C_{1-2}$)-amino, mono- and dialkyl ($C_{1-2}$)-amido, ($C_{1-3}$)-alkoxycarbonyl, trifluoromethylsulfonyl, sulfamoyl,($C_{1-3}$)-alkylsulfonyl, carboxyl, cyano, carbamoyl, ($C_{1-3}$)-dialkylaminosulfonyl, ($C_{1-3}$)-monoalkylamino-sulfonyl and acetyl groups; and $R_2$ and $R_3$ have the meanings as given in claim 1.

3. A compound as claimed in claim 1 and having Formula (I), or a stereoisomer or a pharmacologically acceptable salt thereof, wherein:

R and $R_1$ each independently represent a phenyl group substituted with 1-4 substituents which are the same or different, and are chosen from methyl, methoxy, halogen, trifluoromethyl and cyano, or R and $R_1$ each independently represent a phenyl, thienyl or pyridyl group, which phenyl group is optionally substituted with 1-4 substituents, which are the same or different and are chosen from methyl, methoxy, halogen, trifluoromethyl and cyano;

$R_2$ represents a hydrogen atom or a branched or unbranched $C_{1-8}$ alkyl group;

$R_3$ represents a group $NR_4R_5$, wherein $R_4$ and $R_5$ together, with the nitrogen atom to which they are bonded, form a saturated or unsaturated, monocyclic or bicyclic, heterocyclic moiety having 4 to 10 ring atoms, wherein the heterocyclic group contains one or two heteroatoms chosen from O, N, and S, which heteroatoms can be the same or different, and wherein the heterocyclic moiety is optionally substituted with a branched or unbranched $C_{1-3}$ alkyl, hydroxy or trifluoromethyl group or a fluoro atom.

4. A pharmaceutical composition comprising at least one pharmacologically active compound of Formula (I) according to claim 1, or a stereoisomer or a pharmacologically acceptable salt thereof.

* * * * *